United States Patent [19]
Diefenbacher et al.

[11] Patent Number: 6,027,466
[45] Date of Patent: Feb. 22, 2000

[54] ADJUSTABLE ORTHOPEDIC DEVICE JOINT

[76] Inventors: Beat Diefenbacher, RR 2, Crysler, Ontario, Canada, K0A 1R0; Anthony C. Tyrrell, 1861 SW. 55th Ave., Plantation, Fla. 33317

[21] Appl. No.: 09/148,233

[22] Filed: Sep. 4, 1998

[51] Int. Cl.[7] .............. A61F 5/00; A61F 13/00
[52] U.S. Cl. ...................................... 602/16; 602/26
[58] Field of Search ....................... 602/5, 16, 23–26

[56] References Cited

U.S. PATENT DOCUMENTS

| | | | |
|---|---|---|---|
| 4,881,532 | 11/1989 | Borig et al. | 602/24 X |
| 5,302,169 | 4/1994 | Taylor | 602/16 |
| 5,421,810 | 6/1995 | Davis et al. | 602/26 X |
| 5,669,873 | 9/1997 | Towsley | 602/16 X |
| 5,766,140 | 6/1998 | Tillinghast, III et al. | 602/16 |
| 5,860,943 | 1/1999 | Bloedav et al. | 602/16 |

Primary Examiner—Richard J. Apley
Assistant Examiner—Denise Pothrer
Attorney, Agent, or Firm—Alvin S. Blum

[57] ABSTRACT

An orthopedic joint for connection between first and second body parts provides for free movement in a flexion/extension plane between adjustable stops. The joint further provides for continuous adjustment of an abduction angle. The adjustment can be made while the device is mounted on a wearer, and the adjustment will move the second body part for enhanced adjustability.

6 Claims, 3 Drawing Sheets

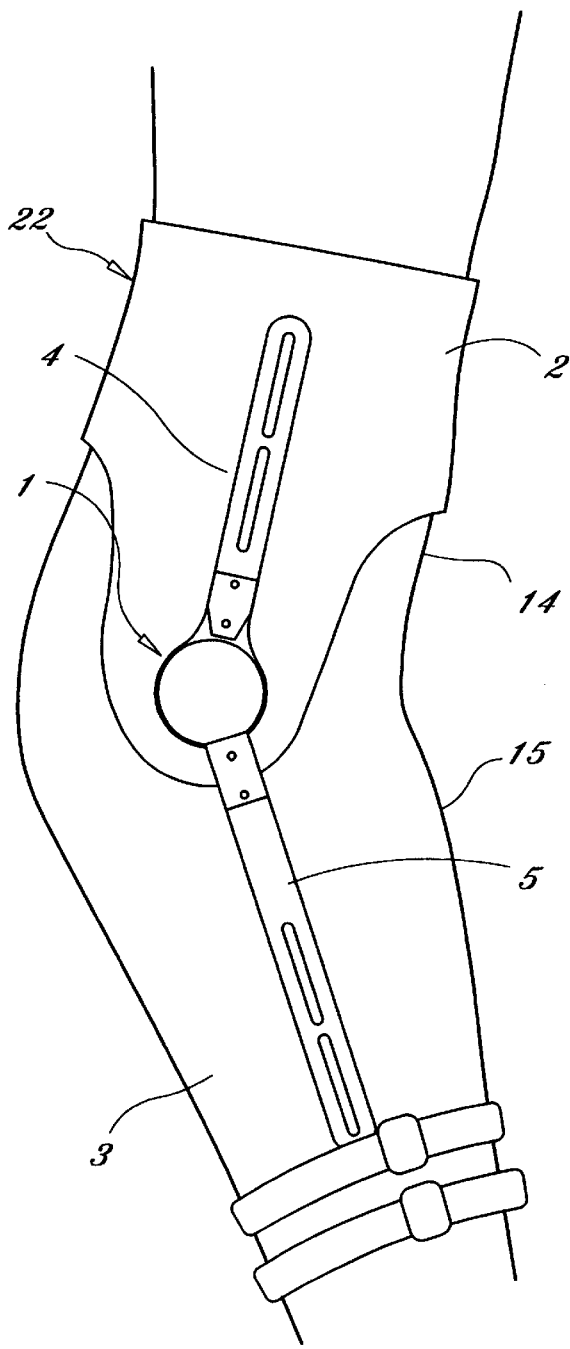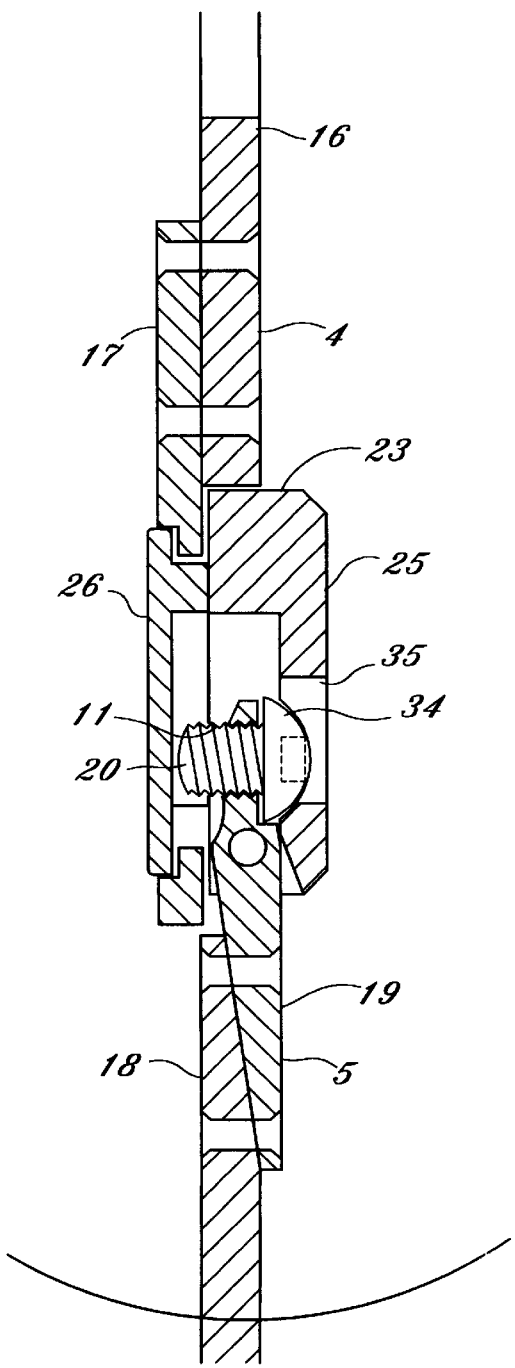
FIG. 1
FIG. 5

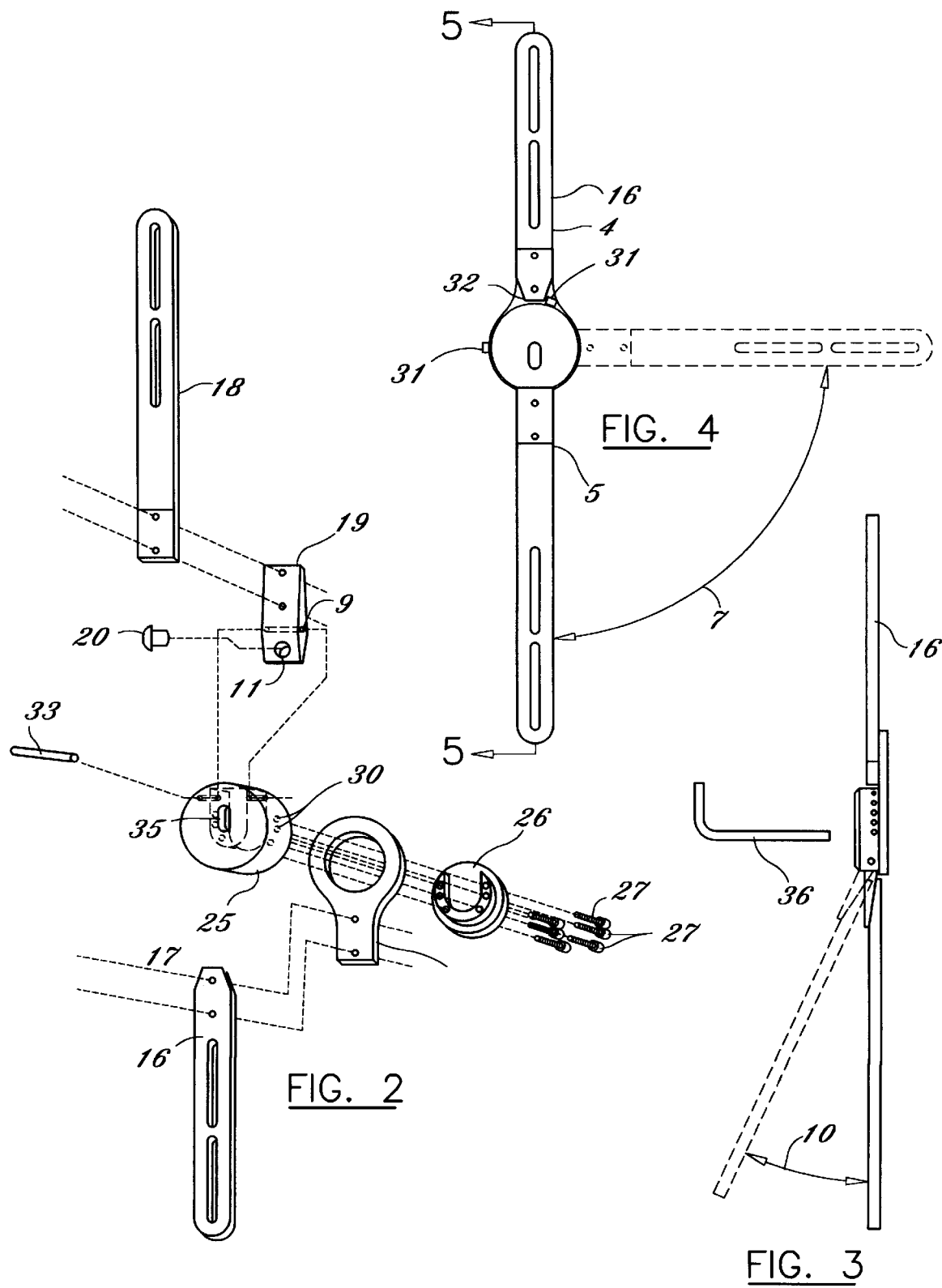

ADJUSTABLE ORTHOPEDIC DEVICE JOINT

BACKGROUND OF THE INVENTION

This invention relates to orthotic devices for limbs and more particularly to a joint for a brace that permits extension and flexion through an adjustable angle and also provides means for continuously adjustably fixing an abduction angle while being worn on the limb.

Davis et al. in U.S. Pat. No. 5,421,810 issued Jun. 6, 1995 teach a hinge having a continuously adjustable stop at one end of the extension-flexion rotation. They provide discontinuous means for adjustment of the fixed abduction angle that requires releasing the joint connection, moving the limb to the desired angle, and then tightening the connection. Using matching gear teeth limits the adjustment to discrete angles.

Williamson et al. in U.S. Pat. No. 5,368,552 issued Nov. 29, 1994 provide an excellent review of the art and disclose a ball and socket connection in the joint to allow another degree of rotation.

Borig et al. in U.S. Pat. No. 4,881,532 issued Nov. 21, 1989 disclose a joint in which there is free abduction motion through a limited angle.

When fitting a brace, especially a hip brace after surgery, the physician will often prescribe a fixed abduction angle to reduce stress on the joint, especially when sitting. When fabricating the brace, it is difficult to predict what the actual abduction angle will be until it is mounted on the body.

If it is not as prescribed, it must be removed, adjusted and mounted again. When the angle is to be changed for some clinical reason, the process must be repeated. When fitting the brace, it is often tempting to disregard small deviations from the required abduction angle. The same holds true for adjustments of the flexion/extension angular extremes. It would be useful to have a joint in which the fixed abduction angle could be continuously adjusted after the brace is mounted on the patient, and where adjustment could be easily made.

SUMMARY OF THE INVENTION

It is accordingly an object of the invention to provide an orthotic joint in which the extremes of flexion and extension are adjustable while the brace is mounted on the body. It is another object of the invention that the fixed abduction angle be continuously adjustable while the brace is mounted on the body. It yet another object that the limb be moved by the abduction adjustment so as to relieve the fitting process from extensive patient cooperation.

The joint of the invention connects a first attachment to a first body part such as the pelvis to a second attachment to a second body part such as the thigh in a brace for supporting the hip joint for example. The joint provides: a housing; a first connector between the housing and the first attachment; and a second connector between the housing and the second attachment. The first connector is pivotally connected to the housing to provide rotary motion restricted to a first, flexion/extension plane. A mechanism is further provided to adjustably limit the angle through which the motion in the first plane is allowed. The second connector is pivotally connected to the housing for rotation limited to movement in a second, abduction/adduction plane that is orthogonal to the first plane. An adjustment is further provided for continuously moving the second connector through the second plane and fixing the abduction angle while the brace is mounted on the body to facilitate adjustment.

These and other objects, features and advantages of the invention will become more apparent when the detailed description is studied in conjunction with the drawings in which like reference characters refer to like elements in the various drawing figures.

BRIEF DESCRIPTION OF THE DRAWINGS

FIG. 1 is a side elevation view of a hip brace in use incorporating the joint of the invention.

FIG. 2 is an exploded perspective view of the joint.

FIG. 3 is a side view of the joint.

FIG. 4 is a top view of the joint.

FIG. 5 is a sectional view taken through line 5—5 of FIG. 4.

DETAILED DESCRIPTION OF THE PREFERRED EMBODIMENT

Figure 6:
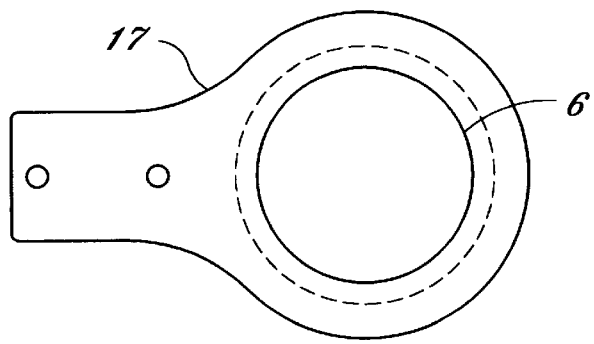
FIG. 6 is a top view of the first connector.

Referring now first to FIG. 1, a hip brace 22 is shown mounted on a patient such as might be used after hip joint repair or replacement surgery to support the joint and limit the limb motion to positions that will not adversely affect healing. Then sitting, it is very important that adduction be limited, because it can cause the joint to dislocate. The hip joint must be free to flexion and extension, but only through a limited angular range.

The brace 22 includes a first body part attachment 2 strapped around the pelvis 14 and a second body part attachment 3 strapped around the thigh 15. Joint 1 pivotally joins the two attachments 2 and 3, providing rotary motion limited to a flexion/extension plane therebetween, by connectors 4 and 5, respectively.

Figure 10:
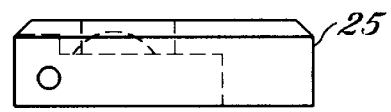
FIG. 10 is a side view of the body portion of the housing.
Figure 7:
FIG. 7 is a side view of the first connector of FIG. 6.
Figure 11:
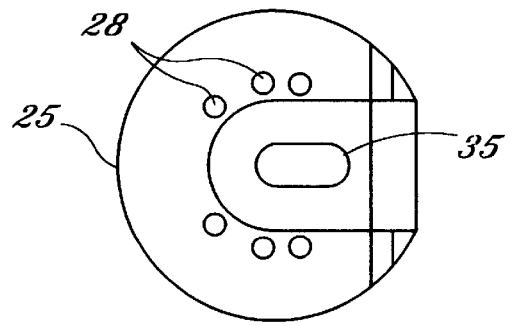
FIG. 11 is a top view of the body portion of FIG. 10.
Figure 8:
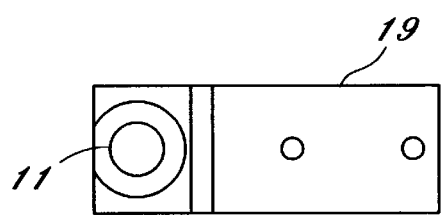
FIG. 8 is a top view of the rocker arm portion of the second connector.
Figure 12:
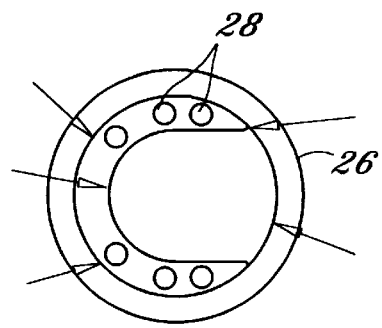
FIG. 12 is a top view of the backing plate portion of the housing.
Figure 9:
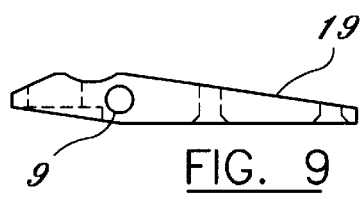
FIG. 9 is a side view of the rocker arm of FIG. 8.
Figure 13:
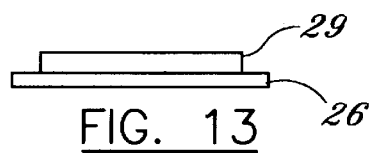
FIG. 13 is a side view of the backing plate of FIG. 12.

Referring now to FIGS. 2–13, the joint 1 will be described in more detail.

A housing 23 is comprised of a body portion 25 and a backing plate 26 joined together by bolts 27 in holes 28. Connector 4 is comprised of a slotted bar first end 16 for affixing to the first body part attachment and a second end 17 with an inner cylindrical passage 6 that cooperates with the outer surface of cylindrical projection 29 of backing plate 26 to form a rotary connection therebetween. The second end 17 is held captive when body and backing plate are joined together, limiting motion to the flexion/extension plane 7. The body 25 is provided with many radial threaded holes 30. Bolts 31 are screwed into selected ones of holes 30 to adjustably limit flexion rotation angle as they engage projection 32 of bar 16.

Connector 5 is comprised of slotted bar 18 that is the first terminus for affixing to the second body attachment and a rocker arm or second terminus 19 that is pivotally mounted in the housing by axle 33 to rotate through an abduction/adduction plane 10, the axle cooperating with cylindrical passage 9 in rocker arm 19. The axis of rotation about axle 33 is orthogonal to the axis of rotation about cylindrical projection 29 so that the plane of abduction is substantially orthogonal to the flexion plane. Spaced away from the axle is a threaded passage 11 in rocker arm 19 perpendicular to the axis of passage 9. A threaded cylinder 20 with a socket head 34 is threaded into passage 11. It is held captive between the body 25 and backing plate 26, while access to the head 34 is provided through slot 35 in the body. This permits the adjustment of the abduction angle while the brace is mounted on the wearer. The leverage is great enough that rotation of cylinder 20 with a wrench 36 causes the abduction angle to change and moves the limb to which the brace is attached to greatly facilitate adjustment. The abduction angle is continuously adjustable and whatever angle is set by cylinder 20 remains fixed until cylinder 20 is readjusted.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. An orthopedic joint for connection between a first body part attachment and a second body part attachment, the joint comprising:
    A) first connector means for attaching to said first body part attachment;
    B) second connector means for attaching to said second body part attachment;
    C) pivot means for connecting said first and second connector means for rotary movement in a first plane for flexion and extension movement between the first and second body part attachments;
    D) stop means operatively connected to said pivot means for adjustably limiting said flexion and extension movement;
    E) rotary attachment means interposed between said first and second connector means for providing rotary motion between said first and second connector means in a second plane substantially orthogonal to said first plane; and
    F) infinitely variable adjustment means connected to said rotary attachment means for moving the relative position between said first and second connector means in said second plane, said adjustment means constructed to maintain an adjusted fixed position of the second connector means when in use and during adjustment.

2. The joint according to claim 1, in which the first body part attachment is constructed for attachment to the pelvis and the second body part attachment is constructed for attachment to the thigh of a person and in which movement of said adjustment means is capable of moving the thigh through said second plane when the first and second body part attachments are mounted on the person.

3. The joint according to claim 2, in which said adjustment means operates by rotation.

4. A joint between a first body part attachment and a second body part attachment in an orthopedic device for supporting an articulation between first and second body parts to permit flexion and extension motion in a first plane, the joint comprising:
    A) a first connector means having a first end for connection to said first body part attachment and a second end;
    B) a second connector means having a first terminus for connection to said second body part attachment and a second terminus;
    C) a housing;
    D) a first pivotal connection between said housing and said second end of said first connector means for pivoting motion about a first axis transverse to said first plane;
    E) a stop means connected to said first pivotal connection for adjustably limiting range of motion through said first plane;
    F) a second pivotal connection between said housing and said second terminus of said second connector means for pivoting about a second axis that is transverse to said first axis for motion in a second plane; and
    G) an infinitely variable adjusting means connecting said housing and said second terminus spaced away from said second axis for moving said second connector means through said second plane by operator adjustment of said adjusting means and for moving said second body part attachment and the body part attached thereto, said adjusting means fixing position of said second connector means in said second plane during adjustment.

5. The joint according to claim 4, in which said adjusting means comprises a rotatable cylinder threadedly engaging said second terminus and held captive in said housing, said cylinder being accessible and rotatable from outside said housing when mounted for use.

6. A joint between a first body part attachment and a second body part attachment in an orthopedic device for supporting an articulation between first and second body parts to permit flexion and extension motion in a first plane, the joint comprising:
    A) a first connector means having a first end for connection to said first body part attachment and a second end;
    B) a second connector means having a first terminus for connection to said second body part attachment and a second terminus;
    C) a housing;
    D) a first pivotal connection between said housing and said second end of said first connector means for pivoting motion about a first axis transverse to said first plane;
    E) a stop means connected to said first pivotal connection for adjustably limiting range of motion in said first plane;
    F) a second pivotal connection between said housing and said second terminus of said second connector means for pivoting about a second axis for motion in a second plane that is transverse to said first plane; and
    G) infinitely variable rotary adjustment means connecting said housing and said second terminus for continuously moving said second connector means through said second plane, and for continuous movement of said second body part attachment and the body part attached thereto, by operator rotation of said rotary adjustment means, said rotary adjustment means fixing position of said second connector means in said second plane at any position of adjustment during said operator rotation.

* * * * *